United States Patent
Greve et al.

[11] 3,931,314
[45] Jan. 6, 1976

[54] BENZOPHENONE DERIVATIVES AND PROCESS FOR THEIR PRODUCTION

[75] Inventors: Heinz Günter Greve; Klaus Resag, both of Frakfurt am Main-Fechenheim, Germany

[73] Assignee: Cassella Farbwerke Mainkur Aktiengesellschaft, Frankfurt am Main-Fechenheim, Germany

[22] Filed: Aug. 26, 1974

[21] Appl. No.: 500,246

Related U.S. Application Data

[62] Division of Ser. No. 358,455, May 8, 1973.

[30] Foreign Application Priority Data

May 12, 1972 Luxemburg............................ 65340

[52] U.S. Cl............................. 260/562 N; 260/562
[51] Int. Cl.²........................................ C07C 103/34
[58] Field of Search ........ 260/562 N, 562 K, 562 P, 260/562 A

[56] References Cited
UNITED STATES PATENTS

| | | | |
|---|---|---|---|
| 3,334,100 | 9/1967 | Zenitz............................ | 260/562 N |
| 3,429,874 | 2/1969 | Topliss............................ | 260/562 N |
| 3,729,470 | 4/1973 | Vaille............................ | 260/562 N |

*Primary Examiner*—C. Davis
*Attorney, Agent, or Firm*—Francis M. Crawford

[57] ABSTRACT

The present invention relates to pharmacologically valuable new benzophenone derivatives having a pronounced sedative action on the central nervous system and some of which also possess muscle-relaxing and aggression-inhibiting properties. These new derivatives have the structural formula

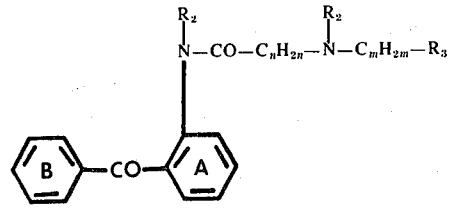

and their acid addition salts, in which $R_1$ and $R_2$ are substituents selected from the group consisting of hydrogen, saturated and unsaturated alkyl groups having 1-4 carbon atoms; $R_3$ is a substituent selected from the group consisting of —CN, —CONH$_2$, —COOCH$_3$, —COOC$_2$H$_5$, —COOH, and —COOMe, where Me is a metallic cation; n is an integer selected from 1 and 2; and m is an integer selected from 1,2, and 3, and wherein the rings A and B may be substituted, ring A being substituted preferably with a halogen such as chlorine or with nitro, trifluoromethyl, methyl, methoxy or methylmercapto, preferably in the 5 position, and ring B being preferably substituted in the 2' position with chlorine or fluorine. The radicals $R_1$ and $R_2$ preferably signify hydrogen or a methyl group, or a n-butyl group in the case of Ring B.

2 Claims, No Drawings

BENZOPHENONE DERIVATIVES AND PROCESS FOR THEIR PRODUCTION

The present application is a division of our U.S. Ser. No. 358,455, filed May 8, 1973.

The invention relates to pharmacologically valuable new benzophenone derivatives of the general formula I

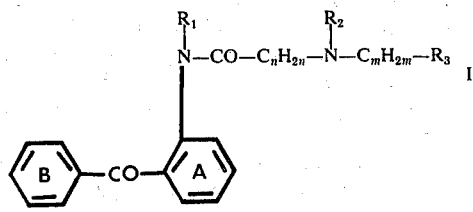

and their acid addition salts, in which
$R_1$ and $R_2$ signify hydrogen or a saturated or unsaturated alkyl radical with 1 to 4 carbon atoms,
$R_3$ signifies a $-CN$, $-CONH_2$, $-COOCH_3$, $-COOC_2H_5$, $-COOH$ or $-COOMe$ group, Me signifying a metal cation,
$n$ is 1 or 2,
$m$ is 1, 2 or 3,
and the rings A and B may be substituted.

Preferred substituents for the ring A are halogen, especially chlorine, nitro, trifluoromethyl, methyl, methoxy or methylmercapto, and substitution is preferably in the 5 position, and preferred substituents for the ring B are fluorine or chlorine, substitution preferably being at the 2' position. The radicals $R_1$ and $R_2$ preferably signify hydrogen or a methyl group, or an n-butyl group in the case of $R_2$.

The metal cation Me is preferably a pharmacologically acceptable metal cation, for example the sodium, potassium, ammonium or calcium.

The invention also extends to processes for the production of compounds of the general formula I.

Compounds of the general formula I may be produced by reacting a benzophenone derivative of the general formula II

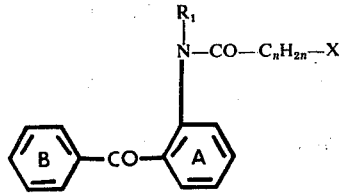

with a compound of the general formula III
$$Y - C_mH_{2m} - R_3 \qquad III$$
one of X and Y signifying the radical $R_2-NH-$ and the other signifying a halogen atom, preferably a bromine or chlorine atom, so as to form a compound of the general formula I with the elimination of H—Hal, $R_1$, $R_2$, $R_3$, $n$ and $m$ being as defined above and the rings A and B being optionally substituted as discussed above. The hydrogen halide which is eliminated is advantageously bound by the addition of an acid-binding agent. Suitable acid-binding agents are a molar excess of the amine used in the reaction or, for example, triethylamine, dimethylaniline, potassium or sodium carbonate or sodium bicarbonate. The amine can also be employed in the form of an acid addition salt, in which case it is then necessary in order to liberate the amine to use a further mole of the acid binding agent. The reaction is carried out in a suitable solvent, preferably at an elevated temperature, typically the reflux temperature of the solvent used. Examples of suitable solvents are ethers, for example dioxane, hydrocarbons, for example benzene, toluene or xylene and ketones, for example acetone or methylisobutylketone. It may be advantageous to carry out the reaction under an inert atmosphere, for example under nitrogen.

Starting compounds of the general formula II, in which X signifies a halogen atom, can easily be produced from aminobenzophenones of the general formula IV

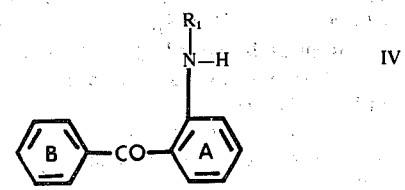

by reaction with a halogenacyl halide of the general formula V

The initial compounds of the general formula II, in which X signifies the radical $R_2 - NH -$, can be obtained by reacting a compound of the general formula IIa

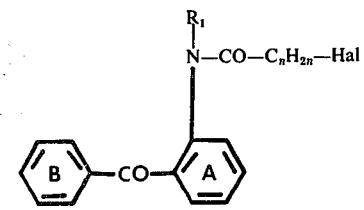

with an amine of the general formula VI
$$R_2 - NH_2$$

The reaction is preferably carried out at a temperature between 5° and 50° with a reaction time of from a few hours up to several days, advantageously in a suitable solvent.

Those compounds of the general formula I, in which $m$ signifies 2 or 3 and $R_1$, $R_2$, $R_3$ and $n$ are as defined above, may be produced by an addition reaction between a benzophenone derivative of the general formula II, in which X signifies $R_2 - NH -$, and a compound containing an aliphatic double bond and of the general formula VII
$$C_mH_{2m-1} - R_3 \qquad VII$$
in which $m$ means the number 2 or 3. The reaction is preferably carried out in a suitable solvent at room temperature or elevated temperature. Examples of suitable solvents are alcohols, ethers, ketones, hydrocarbons and acid amides.

Those compounds of the general formula I in which $R_3$ is CN and is in the α position in relation to the amino group of the side chain can also be prepared by reacting a compound of the general formula II, in which X signifies the radical $R_2 — NH —$, with am aldehyde or ketone of the general formula VIII $$C_mH_{2m}O \qquad \text{VIII}$$

and hydrocyanic acid or an alkali metal cyanide, preferably potassium cyanide. It is normally advantageous first to add the aldehyde or ketone of general formula VIII to an aqueous sodium bisulphite solution as in a Knoevenagel-Bucherer reaction, then to introduce the compound of general formula II, and finally a concentrated aqueous solution of alkali cyanide. The reaction is carried out at room temperature or slightly elevated temperature.

Compounds according to the invention in which $R_3$ signifies a carbmethoxy or carbethoxy group can be converted by saponification into compounds according to the invention in which $R_3$ is —COOH or by ammonolysis into compounds according to the invention in which $R_3$ is —CONH$_2$.

Compounds according to the invention in which $R_3$ is —COOH may be used to prepare the corresponding salts —COOMe.

Normally compounds according to the invention are oily substances which provide crystalline acid addition salts.

The compounds of the general formula I and their pharmaceutically acceptable salts are characterised by valuable pharmacological properties, especially a pronounced sedative action on the central nervous system. Some of these compounds also possess muscle-relaxing and aggression-inhibiting properties. The compounds of the general formula I and their pharmaceutically acceptable salts are therefore valuable pharmaceutical products which can be used as medicaments in the form of pharmaceutical preparations. The pharmaceutical preparations can be put up, for example, as tablets, suppositories, capsules, emulsions or suspensions in a known manner by the use of pharmaceutically acceptable diluents or carriers which do not react with the compounds. As diluents or carriers it is possible to use any substance which is suitable for the purpose in mind, for example talcum, starch, vegetable oils or petroleum jellies. If desired the pharmaceutical preparations may also contain other therapeutically active substances.

The pharmacological investigation of the sedative action on the central nervous system was carried out using the climbing tests on albino mice described by P. K. KNEIP: Arch. int. pharmacodyn 126, 238 (1960) and R. DOMENJOZ and W. THEOBALD: Arch. int. pharmacodyn 120, 450 (1959).

In the table which follows, the results of the pharmacological investigations carried out are summarised. In the last table under the heading "Sedative action %" there is given the percentage of the experimental animals which no longer take up the normally readily assumed climbing work.

| Compound | LD$_{50}$ g/kg (mouse) | | Dose mg/kg p.o. | Sedative action % |
|---|---|---|---|---|
| 2-(5-Cyano-N,4-dimethyl-3-aza-pentanamido)-5-chlor-benzophenone | 0.315 | i.p. | 8 | 50 |
| 2-(5-Cyano-3-aza-hexanamid0)-5-chlor-benzophenone | 0.6 | i.p. | 8 | 50 |
| 2-(5-Cyano-N,3-dimethyl-3-aza-hexanamido)-5-nitro-benzophenone | 1.1 | p.o. | 10 | 60 |
|  | 0,48 | i.p. |  |  |
| 2-(5-Cyano-N,4-dimethyl-3-aza-pentanamido)-benzophenone | 0.32 | i.p. | 8 | 70 |
| 2-(5-Cyano-3-allyl-3-aza-pentanamido)-2'-5-dichlor-benzophenone | 0.63 | i.p. | 8 | 60 |
| 2-(5-Cyano-N-methyl-3-n-butyl-3-aza-pentanamido)-5-chlor-benzophenone | 0.36 | i.p. | 8 | 80 |
| 2-(5-Cyano-N-methyl-3-n-butyl-3-aza-pentanamido)-5-nitro-benzophenone |  |  | 8 | 50 |
|  | 0.68 | i.p. |  |  |
| 2-(5-Cyano-N,4-dimethyl-3-aza-pentanamido)-5-methoxy-benzophenone | 0.25 | i.p. | 8 | 60 |
| 2-(5-Cyano-N,4-dimethyl-5-aza-pentanamido)-5-methyl-benzophenone | 0.3 | i.p. | 8 | 70 |
| 2-(4-Cyano-N-methyl-3-aza-butanamido)-5-chlor-benzophenone | 0.17 | i.p. | 8 | 60 |
| 2-(5-Cyano-N,3-dimethyl-3-aza-pentanamido)-5-chlor-benzophenone |  |  | 8 | 50 |
|  | 0.24 | i.p. |  |  |
| 2-(5-Cyano-N,3,4-trimethyl-3-aza-pentanamido)-5-chlor-benzophenone | 0.32 | i.p. | 9 | 50 |
| 2-(5-Cyano-N,3-dimethyl-3-aza-pentanamido)-5-nitro-benzophenone | >1.0 | p.o. | 10 | 50 |
| 2-(5-Cyano-4-methyl-3-aza-pentanamido)-benzophenone | >1.0 | p.o. | 10 | 50 |
| 2-(6-Cyano-3-methyl-3-aza-hexanamido)-5-chlor-benzophenone |  |  | 8 | 60 |
| 2-(5-Cyano-N-methyl-3-aza-pentanamido)-5-methoxy-benzophenone |  |  | 8 | 50 |
| 2-(5-Cyano-N-methyl-3-aza-pentanamido)-5-methyl-benzophenone |  |  | 8 | 50 |

-continued

| Compound | LD₅₀ g/kg (mouse) | | Dose mg/kg p.o. | Sedative action % |
|---|---|---|---|---|
| 2-(5-ethoxycarbonyl-N-methyl-3-aza-pentanamido)-5-trifluormethyl-benzophenone | 0.4 | i.p. | 8 | 60 |
| 2-(5-Carboxy-3-methyl-3-aza-pentanamido)-5-chlor-benzophenone | 0.45 | i.p. | 8 | 90 |
| 2-(6-ethoxycarbonyl-N-methyl-3-aza-hexanamido)-5-nitro-benzophenone | 0.65 | i.p. | 8 | 60 |
| 2-(4-Methoxycarbonyl-N-methyl-3-aza-butanamido)-5-chlor-benzophenone | 0.95 | p.o. | 10 | 50 |
| 2-(6-ethoxycarbonyl-3-aza-hexanamido)-5-nitro-benzophenone | | | 8 | 50 |
| 2-(5-ethoxycarbonyl-3-aza-pentanamido)-2',5-dichlor-benzophenone | | | 8 | 70 |
| 2-(5-ethoxycarbonyl-N-methyl-3-aza-pentanamido)-5-methylmerkapto-benzophenone | | | 8 | 60 |
| 2-(5-ethoxycarbonyl-N-methyl-3-aza-pentanamido)-5-methyl-benzophenone | | | 8 | 50 |
| Comparative preparation Meprobamate | 0.62 | i.p. | 70 | 50 |

In the following examples the temperatures are given in °C. The abbreviation "Z" in the statements of the melting points means decomposition. The sorbent used for the thin layer chromatograms was silica gel HF 254 + 366 (Type 60) according to Stahl. The proportions given in the case of the eluents are proportions by volume.

EXAMPLE 1

9.8 g of 3-methylamino-2-methylpropionitrile were dissolved in 100 mls. of anhydrous dioxane. A weak stream of nitrogen was passed into this solution and it was heated to boiling under reflux. A solution of 16.1 g of 2-(2-chloro-N-methyl-acetamido)-5-chlorobenzophenone, dissolved in 150 mls. of anhydrous dioxane, was then added drop by drop whilst stirring, and the reaction mixture was heated under reflux for 4 hours. After cooling, the precipitated 3-methylamino-2-methylpropionitrile hydrochloride was filtered off under suction and the filtrate was concentrated in vacuo. The oily residue (20.0g) was dissolved in 300 mls. of absolute diethyl ether, filtered and the monohydrochloride of 2-(5-cyano-N,3-dimethyl-3-aza-hexanamido)-5-chlorobenzophenone was precipitated with dry hydrogen chloride. The yield was 18.8g, corresponding to 89% of theory. The product had a melting point of 113°–115° and was analytically pure without re-crystallisation. A thin-layer chromatogram of a sample of the product showed an absence of the starting compound and the RF value of the product was 0.85 in methanol.

EXAMPLE 2

3.4 g of 2-(methylamino-acetamido)-5-chlorobenzophenone hydrochloride, 0.75 g of chloracetonitrile and 2.0 g of triethylamine were heated with agitation under reflux for 8 hours in 100 mls. of absolute toluene. The triethylamine hydrochloride with was precipitated when the reaction mixture was cooled overnight was filtered off, and the filtrate was washed using 100 mls. of water each time, dried over potassium carbonate, filtered and concentrated in vacuo. The 3.5 g of oily base obtained were dissolved in 120 mls. of anhydrous ether, filtered and 2-(4-cyano-3-methyl-3-azabutyramido)-5-chlorobenzophenone hydrochloride with a melting point of 152°–154° was obtained in a yield of 3.2 g, corresponding to 84.5% of theory, by passing in dry hydrogen chloride. In a thin layer chromatogram the RF value in 2:8 cyclohexane/ethyl acetate as flow medium was 0.9.

EXAMPLE 3

3.3 g of 2-(2-Chloro-N-methyl-acetamido)-5-nitrobenzophenone, 1.2 g of 3-amino-butyronitrile hydrochloride and 2.0 g of triethylamine were heated in 100 mls. of anhydrous benzene for 4 hours while stirring and boiling under reflux. After cooling to room temperature the precipitated triethylamine hydrochloride was filtered off under suction and the filtrate was shaken three times with 100 mls. of water each time in a separating funnel, dried over potassium carbonate, filtered and concentrated in vacuo.

3.3 g of oily base obtained were dissolved in 150 mls. of anhydrous diethyl ether, the solution was filtered, and the monohydrochloride of 2-(5-cyano-N,4-dimethyl-3-aza-pentanamido)-5-nitro-benzophenone was obtained by passing dry hydrogen chloride into the solution. The yield was 2.9 g corresponding to 70% of theory, the melting point was 129°–131°, and the RF value in methanol as flow medium was 0.75.

By methods similar to those described in Examples 1, 2 and 3, the compounds set out in the following Table I were also synthesised:

TABLE I

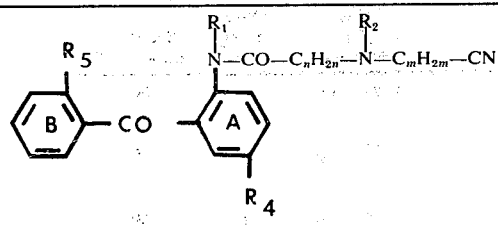

| | $R_1$ | $C_nH_{2n}$ | $R_2$ | $C_mH_{2m}$ | $R_4$ | $R_5$ | Melting point of the hydrochloride |
|---|---|---|---|---|---|---|---|
| 1 | $CH_3$ | $-CH_2-$ | H | $-CH_2-CH_2-$ | Cl | H | 144 – 146° |
| 2 | $CH_3$ | $-CH_2-$ | H | $-CH_2-CH(CH_3)-$ | Cl | H | 145 – 147° |
| 3 | $CH_3$ | $-CH_2-$ | H | $-CH(CH_3)-CH_2-$ | Cl | H | 131 – 133° |
| 4 | $CH_3$ | $-CH_2-$ | H | $-CH_2-$ | Cl | H | 147 – 149° |
| 5 | H | $-CH_2-$ | H | $-CH_2-CH(CH_3)-$ | Cl | H | 183 – 185° |
| 6 | H | $-CH_2-$ | H | $-CH(CH_3)-CH_2-$ | Cl | H | 175 – 177° |
| 7 | $CH_3$ | $-CH_2-$ | $CH_3$ | $-CH_2-CH_2-$ | Cl | H | 184 – 186° |
| 8 | H | $-CH_2-$ | H | $-CH_2-CH_2-$ | Cl | H | 146 – 148° |
| 9 | H | $-CH_2-$ | $CH_3$ | $-CH_2-CH(CH_3)-$ | Cl | H | 136 – 138° |
| 10 | H | $-CH_2-$ | $CH_3$ | $-CH_2-CH_2-$ | Cl | H | 165 – 167° |
| 11 | $CH_3$ | $-CH_2-$ | $CH_3$ | $-CH(CH_3)-CH_2-$ | Cl | H | 140 – 142° |
| 12 | $CH_3$ | $-CH_2-CH_2-$ | H | $-CH(CH_3)-CH_2-$ | Cl | H | 153 – 155° |
| 13 | $CH_3$ | $-CH_2-$ | H | $-CH_2-CH_2-$ | $NO_2$ | H | 119 – 121° |
| 14 | $CH_3$ | $-CH_2-$ | $CH_3$ | $-CH(CH_3)-CH_2-$ | $NO_2$ | H | 103 – 105° |
| 15 | $CH_3$ | $-CH_2-$ | $CH_3$ | $-CH_2-CH_2-$ | $NO_2$ | H | 80 – 82° |
| 16 | $CH_3$ | $-CH_2-$ | $CH_2-CH=CH_2$ | $-CH_2-CH_2-$ | Cl | H | 121 – 123° |
| 17 | $CH_3$ | $-CH(CH_3)-CH_2-$ | H | $-CH(CH_3)-CH_2-$ | Cl | H | 126 – 128° |
| 18 | $CH_3$ | $-CH_2-$ | $CH_3$ | $-CH_2-CH(CH_3)-$ | $NO_2$ | H | 94 – 96° |
| 19 | $CH_3$ | $-CH_2-$ | H | $-CH_2-$ | $NO_2$ | H | 143 – 145° |
| 20 | H | $-CH_2-$ | H | $-CH(CH_3)-CH_2-$ | $NO_2$ | H | 200 – 202° |
| 21 | $CH_3$ | $-CH_2-CH_2-$ | $CH_3$ | $-CH_2-CH_2-$ | Cl | H | 149 – 152° |
| 22 | H | $-CH_2-$ | H | $-CH_2-CH_2-$ | $NO_2$ | H | 179 – 181° |
| 23 | $CH_3$ | $-CH_2-$ | H | $-CH(CH_3)-CH_2-$ | $CF_3$ | H | 113 – 115° |
| 24 | $CH_3$ | $-CH_2-$ | H | $-CH_2-CH_2-$ | $CF_3$ | H | 137 – 139° |
| 25 | $CH_3$ | $-CH_2-$ | $CH_3$ | $-CH(CH_3)-CH_2-$ | $CF_3$ | H | 145 – 148° |
| 26 | $CH_3$ | $-CH_2-$ | H | $-CH_2-CH(CH_3)-$ | $CF_3$ | H | 129 – 131° |
| 27 | H | $-CH_2-$ | H | $-CH(CH_3)-CH_2-$ | H | H | 132 – 134° |
| 28 | H | $-CH_2-$ | H | $-CH_2-CH(CH_3)-$ | $CF_3$ | H | 143 – 146° |
| 29 | $CH_3$ | $-CH_2-$ | $C_2H_5$ | $-CH_2-CH_2-$ | $NO_2$ | H | 106 – 109° |
| 30 | H | $-CH_2-$ | H | $-CH(CH_3)-CH_2-$ | Cl | Cl | 193 – 195° |
| 31 | $CH_3$ | $-CH_2-$ | $C_2H_5$ | $-CH_2-CH_2-$ | Cl | H | 128 – 130° |
| 32 | $CH_3$ | $-CH_2-CH_2-$ | H | $-CH(CH_3)-CH_2-$ | $NO_2$ | H | 174 – 176° |
| 33 | $CH_3$ | $-CH_2-CH_2-$ | $CH_3$ | $-CH_2-CH_2-$ | $NO_2$ | H | 177 – 179° |
| 34 | $CH_3$ | $-CH_2-$ | $H_2C-CH=CH_2$ | $-CH_2-CH_2-$ | $NO_2$ | H | 139 – 141° |
| 35 | $CH_3$ | $-CH_2-$ | $H_2C-CH=CH_2$ | $-CH_2-CH_2-$ | $CF_3$ | H | 94 – 96°(Z) |
| 36 | $CH_3$ | $-CH_2-$ | $H_2C-CH=CH_2$ | $-CH(CH_3)-CH_2-$ | Cl | H | 109 – 111°(Z) |

TABLE I-continued $$R_5 \text{—} B \text{—} CO \text{—} A \text{—} N(R_1)\text{—}CO\text{—}C_nH_{2n}\text{—}N(R_2)\text{—}C_mH_{2m}\text{—}CN$$
(with $R_4$ on ring A)

| | $R_1$ | $C_nH_{2n}$ | $R_2$ | $C_mH_{2m}$ | $R_4$ | $R_5$ | Melting point of the hydrochloride |
|---|---|---|---|---|---|---|---|
| 37 | $CH_3$ | $-CH_2-$ | $H_2C-CH=CH_2$ | $-CH(CH_3)-CH_2-$ | $NO_2$ | H | 102 – 104°(Z) |
| 38 | $CH_3$ | $-CH_2-$ | H | $-CH(CH_3)-CH_2-$ | H | H | 126 – 128° |
| 39 | $CH_3$ | $-CH(CH_3)-CH_2-$ | $CH_3$ | $-CH_2-CH_2-$ | Cl | H | 151 – 153° |
| 40 | $CH_3$ | $-CH(CH_3)-CH_2-$ | $CH_3$ | $-CH_2-CH_2-$ | $NO_2$ | H | 97 – 100° |
| 41 | H | $-CH_2-$ | H | $-CH_2-CH_2-$ | Cl | Cl | 142 – 144° |
| 42 | H | $-CH_2-$ | $H_2C-CH=CH_2$ | $-CH_2-CH_2-$ | Cl | Cl | 128 – 130° |
| 43 | $CH_3$ | $-CH_2-$ | $CH_3$ | $-CH_2-CH_2-CH_2-$ | Cl | H | 143 – 145° |
| 44 | H | $-CH_2-$ | $CH_3$ | $-CH_2-CH_2-CH_2-$ | Cl | H | 164 – 167°(Z) |
| 45 | $H_2C-CH=CH_2$ | $-CH_2-$ | H | $-CH(CH_3)-CH_2-$ | Cl | H | 125 – 127° |
| 46 | $H_2C-CH=CH_2$ | $-CH_2-$ | $H_2C-CH=CH_2$ | $-CH_2-CH_2-$ | Cl | H | 128 – 130° |
| 47 | $CH_3$ | $-CH_2-$ | $n-C_4H_9$ | $-CH_2-CH_2-$ | Cl | H | 139 – 141° |
| 48 | $CH_3$ | $-CH_2-$ | $n-C_4H_9$ | $-CH_2-CH_2-$ | $NO_2$ | H | 127 – 129° |
| 49 | $n-C_4H_9$ | $-CH_2-$ | H | $-CH(CH_3)-CH_2-$ | Cl | H | 177 – 179° |
| 50 | $n-C_4H_9$ | $-CH_2-$ | H | $-CH(CH_3)-CH_2-$ | Cl | H | 163 – 165°(Z) |
| 51 | $CH_3$ | $-CH_2-$ | H | $-CH(CH_3)-CH_2-$ | $OCH_3$ | H | 136 – 138° |
| 52 | $CH_3$ | $-CH_2-$ | H | $-CH_2-CH_2-$ | $OCH_3$ | H | 154 – 156° |
| 53 | $CH_3$ | $-CH_2-$ | H | $-HC(CH_3)-CH_2-$ | $SCH_3$ | H | 134 – 136° |
| 54 | $CH_3$ | $-CH_2-$ | H | $-CH(CH_3)-CH_2-$ | $SCH_3$ | H | 145 – 147°(Z) |
| 55 | $CH_3$ | $-CH_2-$ | H | $-CH_2-CH_2-$ | $CH_3$ | H | 152 – 154°(Z) |
| 56 | $CH_3$ | $-CH_2-$ | H | $-CH(CH_3)-CH_2-$ | $CH_3$ | H | 143 – 145° |
| 57 | $CH_3$ | $-CH_2-$ | $C_2H_5$ | $-HC(CH_3)-CH_2-$ | $NO_2$ | H | 123 – 125° |
| 58 | $CH_3$ | $-CH_2-$ | $CH_3$ | $-HC(CH_3)-CH_2-$ | Cl | Cl | 152 – 155°(Z) |
| 59 | $CH_3$ | $-CH_2-$ | $CH_3$ | $-HC(CH_3)-CH_2-$ | Cl | F | 128 – 131° |
| 60 | $n-C_4H_9$ | $-CH_2-$ | $n-C_4H_9$ | $-CH_2-CH_2-$ | Cl | H | 119 – 121° |
| 61 | H | $-CH_2-$ | $n-C_4H_9$ | $-CH_2-CH_2-$ | Cl | Cl | 98 – 100° |

The production of starting compounds of the general formula II, in which X is chlorine or bromine, for use in the foregoing examples is exemplified by the production, described below, of the 2-(N-methyl-N-β-chloropropionylamino)-5-chloro-benzophenone used as starting compound for example in the production of 2-(6-cyano-N,5-dimethyl-4-aza-hexanamido)-5-chloro-benzophenone and 2-(6-cyano-N,4-dimethyl-4-aza-hexanamido)-5-chloro-benzophenone which appear in the table above, when they are produced according to the method of Example 1.

14.0 g of β-chloropropionyl chloride were rapidly added drop by drop to a solution of 24.6 g of 2-methylamino-5-chloro-benzophenone in 300 mls. of anhydrous toluene, the temperature rising from 18° to 25°C. The reaction mixture was then maintained for 4 hours at an internal temperature of 80°C, and then heated for a further 2 hours, with stirring, under reflux. After cooling it is filtered and unreacted β-chloropropionyl chloride was drawn off under vacuum at approximately 0.1 mm Hg using a water bath rising to a final temperature of 90°C. The oily residue was allowed to stand for 3 days in a refrigerator where it crystallised. The crystals were rubbed up with petrol ether and dried in vacuo.

Yield: 29.8 g of 2-(N-methyl-N-β-chloro-propionylamino)-5-chloro-benzophenone (89% of theory) with a melting point of 73°– 75°.

EXAMPLE 4

13.0 g of 2-(chloraceto-methylamido)-5-chlorobenzophenone, 5.0 g of methyl aminoacetate hydrochloride and 8.0 g of triethylamine were heated under reflux in 250 mls. of absolute toluene for 6 hours whilst stirring. The precipitated triethylamine hydrochloride was filtered off under suction after cooling, the filtrate being shaken three times, with 250 mls. of water each time, in a separating funnel, and the organic phase was dried over potassium carbonate, filtered and concentrated in vacuo. The oily residue was dissolved in 300 mls. of absolute ether, filtered and converted into 9.5 g of 2-(4-carbmethoxy-N-methyl-3-aza-butyramido)-5-chlorobenzophenone hydrochloride with a melting point of 116°–118°, corresponding to 58% of theory, by passing in dry hydrogen chloride gas. The RF value in a thin layer chromatogram with 1:1 cyclohexane/ethyl acetate as flow medium was 0.95.

EXAMPLE 5

A mixture of 3.4 g of 2-(methylamino-acetamido)-5-chlorobenzo-phenone hydrochloride, 1.7 g of ethyl bromacetate and 2.0 g of triethylamine was heated to boiling in 100 mls. of absolute toluene for 8 hours whilst stirring. The triethylamine hydrochloride which was precipitated quantitatively was filtered off under suction, the filtrate was shaken three times with 100 mls. of water each time and dried over potassium carbonate. 3.2 g of oily crude base were obtained which, dissolved in 50 mls. of anhydrous ether, were converted into 2-(4-carbethoxy-3-methyl-3-aza-butyramido)-5-chlorobenzophenone hydrochloride by passing in dry hydrogen chloride. The yield amounted to 3.5 g corresponding to 82% theory. The melting point was 177°–179° and the RF value in the thin layer chromatogram was 0.7 in 1:1 cyclohexane/ethyl acetate as flow medium.

EXAMPLE 6

1.7 g of 2-(methylamino-acetamido)-5-chlorobenzophenone hydrochloride, 0.85 g of ethyl bromacetate and 0.7 g of anhydrous potassium carbonate were heated for 20 hours under a reflux in 100 mls. of anhydrous acetone whilst stirring. After cooling, the inorganic salt was filtered off under suction concentrated in vacuo, and the oily residue was dried in vacuo. The yield of oily crude base was 1.4 g. It was dissolved in 30 mls. of absolute dioxane, the solution was filtered and diluted with 30 mls. absolute ether, 1.3 g of 2-(4-carbethoxy-3-methyl-3-aza-butyramido)-5-chlorobenzophenone hydrochloride with a melting point of 178°–180° being obtained by passing in dry hydrogen chloride. The product was identical with that obtained in Example 5.

EXAMPLE 7

A mixture of 2.2 g of 2-(methylamino-acetamido)-5-chloro-benzophenone hydrochloride, 1.2 g of chloracetamide and 2.0 g of triethylamine was heated for 8 hours under a reflux in 100 mls. of anhydrous xylene. The triethylamine hydrochloride which was precipitated quantitatively was filtered off under suction after cooling and the filtrate was shaken three times with 100 mls. of water each time, the organic phase being dried over anhydrous potassium carbonate, filtered and concentrated in vacuo. The oily crude base obtained as a residue (2.2g) was dissolved in 100 mls. of anhydrous diethylether and the solution was filtered. By passing dry hydrogen chloride into the solution 2.0 g of 2-(4-amidocarbonyl-3-methyl-3-aza-butyramido)-5-chlorobenzophenone hydrochloride (74% of theory) were obtained with a melting point of 163°–165° (decomposes).

This product could also be obtained by dissolving 4.0 g of 2-(4-ethoxy-carbonyl-3-methyl-3-aza-butyramido)-5-chlorobenzophenone hydrochloride in 80 mls. of anhydrous ethyl alcohol and whilst stirring at 60° to 70° introducing into the solution for 8 hours a stream of ammonia gas, the reaction mixture being allowed to stand further overnight in a closed vessel and then further processed by filtering off precipitated ammonium chloride and concentrating in vacuo. By proceeding as described in the paragraph above, 2-(4-amidocarbonyl-3-methyl-3-aza-butanamido)-5-chlorobenzophenone hydrochloride was obtained. Yield: 2.5 g (68% of theory). The product possessed a melting point of 162° – 165° (decomposes).

EXAMPLE 8

4.6 g of 2-(methylamino-acetamido)-5-chlorobenzophenone hydrochloride were heated in 100 mls. of dry xylene with 3 g of triethylamine and 1.9 g of chloracetic acid for 8 hours under reflux whilst stirring. After cooling, the precipitated triethylamine hydrochloride was filtered off and the filtrate was shaken 3 times with 100 mls. of water each time. After drying over potassium carbonate and filtering, it was concentrated in vacuo, the oily crude base obtained being dissolved in 100 mls. of dry ether and filtered again. By passing in dry hydrogen chloride gas, filtering under suction and drying in a vacuum desiccator, 2.8 g (71% of theory) of 2-(4-carboxy-3-methyl-3-aza-butyramido)-5-chlorobenzophenone hydrochloride were obtained with a melting point of 162°–164°.

By process similar to those described Examples 4 to 8, the compounds described in the following Table II were also produced:

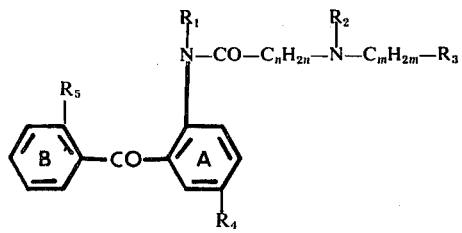

TABLE II

| $R_1$ | $C_nH_{2n}$ | $R_2$ | $R_3$ | $C_mH_{2m}$ | $R_4$ | $R_5$ | Melting point of hydrochloride |
|---|---|---|---|---|---|---|---|
| H | —$CH_2$— | H | CO—$CH_3$ | —$CH_2$— | Cl | H | 128 – 130° |
| $CH_3$ | —$CH_2$— | H | CO—$OC_2H_5$ | —$H_2C$—$CH_2$— | Cl | H | 111 – 113° |

TABLE II-continued

| R₁ | CₙH₂ₙ | R₂ | R₃ | CₘH₂ₘ | R₄ | R₅ | Melting point of hydrochloride |
|---|---|---|---|---|---|---|---|
| H | —CH₂— | H | CO—OC₂H₅ | —H₂C—CH₂— | Cl | H | 105 – 107° |
| CH₃ | —CH₂— | H | CO—OCH₃ | —CH₂— | NO₂ | H | 142 – 144° |
| CH₃ | —CH₂— | H | CO—OC₂H₅ | —CH₂—CH₂— | CF₃ | H | 137 – 139° |
| H | —CH₂— | H | CO—OC₂H₅ | —CH₂—CH₂— | Cl | Cl | 129 – 131° |
| CH₃ | —CH₂— | H | CO—OC₂H₅ | —CH₂—CH₂— | NO₂ | H | 127 – 129° |
| CH₃ | —CH₂— | H | CO—OC₂H₅ | —CH₂—CH₂—CH₂— | Cl | H | 136 – 138° |
| H | —CH₂— | H | CO—OC₂H₅ | —CH₂—CH₂—CH₂— | NO₂ | H | 157 – 159° |
| CH₃ | —CH₂— | H | CO—OC₂H₅ | —CH₂—CH₂—CH₂— | NO₂ | H | 155 – 157° |
| CH₂—CH=CH₂ | —CH₂— | H | CO—OC₂H₅ | —CH₂—CH₂— | Cl | H | 116 – 118° |
| H | —CH₂— | CH₃ | COOH | —CH₂—CH₂— | Cl | H | 154 – 157° |
| CH₃ | —CH₂— | H | CO—OC₂H₅ | —CH₂—CH₂— | OCH₃ | H | 143 – 145° |
| CH₃ | —CH₂— | H | CO—OC₂H₅ | —CH₂—CH₂— | SCH₃ | H | 143 – 145° |
| CH₃ | —CH₂— | H | CO—OC₂H₅ | —CH₂—CH₂— | CH₃ | H | 108 – 111° |
| CH₃ | —CH₂— | H | CO—OC₂H₅ | —CH₂—CH₂—CH₂— | OCH₃ | H | 84 – 86° |
| CH₃ | —CH₂— | H | CO—OC₂H₅ | —CH₂—CH₂—CH₂— | CH₃ | H | 106 – 108° |

EXAMPLE 9

3.0 g of 2-(methylamino-acetamido)-5-chloro-benzophenone were dissolved in 30 mls. of anhydrous alcohol and then mixed with 2.0 g of freshly distilled acrylonitrile. The mixture was stirred for 2 hours at room temperature and then heated under reflux for a further 8 hours. After being allowed to stand overnight at room temperature a further 2.0 g of freshly distilled acrylonitrile was added and the mixture heated under reflux with stirring for a further 4 hours. At this point a sample showed in a thin-layer chromatogram a uniform point which differed from that of the initial product. The turbid solution was filtered and concentrated in vacuo (approx. 0.1 mm Hg), 3.0 g of a colourless oil being obtained. This residue was dissolved in anhydrous diethyl ether. After passing dry hydrogen chloride into this solution 3.6 g of 2-(5-cyano-3-methyl-3-aza-pentanamido)-5-chloro-benzophenone hydrochloride were obtained, corresponding to 92% of theory. The product had a melting point of 166°–168°. The RF value in a thin-layer chromatogram in methanol as flow medium was 0.85.

The RF value and the melting point were identical with those of the product which was obtained from 2-(chloracetamido)-5-chlorobenzophenone and β-methylamino-propionitrile using a method similar to that of Example 1 (cf. 10th example in table in Example 3).

In an analogous manner, starting from 2-methylaminoacetamido)-5-chloro-benzophenone and ethyl acrylate, 2-(5-ethoxycarbonyl-3-methyl-3-aza-pentanamido)-5-chlorobenzophenone hydrochloride is obtained with a melting point of 129°–131°, and starting from 2-(methylamino-acetamido)-5-chlorobenzophenone and acrylamide, 2-(5-amidocarbonyl-3-methyl-3-aza-pentanamido)-5-chloro-benzophenone hydrochloride is obtained with a melting point of 158°–160°.

The 2-(methylamino-acetamido)-5-chloro-benzophenone required as starting compound was produced as follows:

A solution of 24.5 g of 2-(chloracetamido)-5-chlorobenzophenone in 400 mls. of anhydrous dioxane was mixed with 150 mls. of a 15% solution of methylamine in methyl alcohol and was then allowed to stand at room temperature overnight in a closed vessel. The reaction mixture was then filtered and the filtrate is concentrated in vacuo at a waterbath temperature of 25°, the residue being shaken with 630 mls. of diethyl ether and 700 mls. of 0.3N hydrochloric acid. The ether layer was shaken out once again with 250 mls. of 0.3N hydrochloric acid and the combined hydrochloric acid extracts were rendered alkaline with concentrated aqueous ammonia whilst cooling thoroughly, and were then extracted with methylene chloride; the methylene chloride phase was dried over potassium carbonate. After drying the methylene chloride solution was filtered and concentrated in vacuum. The oily crude base obtained as a residue, after drying, was dissolved in 100 mls. of anhydrous diethyl ether, filtered and converted by the introduction of dry hydrogen chloride into 23.8 g of 2-(methylamino-acetamido)-5-chlorobenzophenone hydrochloride (88% of theory), melting point 199°–201°.

EXAMPLE 10

2.1 g of sodium bisulphite were dissolved in 15 mls. of water and mixed drop by drop at 15°–20°C with 1.8 g of 40% formaldehyde solution, the stirring being continued for 30 minutes and then 3.0 g of 2-(methylamino-acetamido)-5-chlorobenzophenone were added to the reaction mixture. Then whilst stirring a solution of 1.3 g of potassium cyanide in 3 mls. of water was added drop by drop and the mixture stirred for 3 hours at 40°C. After being allowed to stand overnight at room temperature, the semi-solid reaction product was filtered off under suction, shaken up several times with water, and dried in a vacuum desiccator. From a solution of 2.4 g of the crude base in 100 mls. of anhydrous diethyl ether, 2.8 g of 2-(4-cyano-3-methyl-3-aza-butanamido)-5-chloro-benzophenone hydrochloride (74% of theory) with a melting point of 153°–155° were obtained by passing in dry hydrogen chloride.

The melting point and the RF value in a thin-layer chromatogram (0.9) correspond with those of the product obtained in Example 2.

What is claimed is:

1. Benzophenone derivative having the structural formula

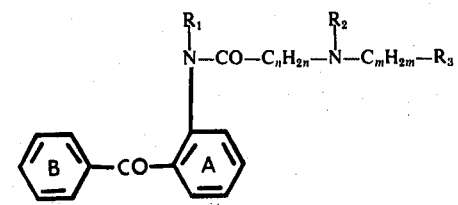

and the acid addition salts thereof, wherein $R_1$ and $R_2$ are substituents selected from the group consisting of hydrogen, saturated and unsaturated alkyl groups having 1 – 4 carbon atoms; $R_3$ is —$CONH_2$; $n$ is an integer selected from 1 and 2; and $m$ is an integer selected from 1, 2 and 3, and wherein the ring A is substituted at the 5-position with a substituent selected from the group consisting of halogen, nitro, trifluoromethyl, methyl, methoxy and methylmercapto and the ring B is substituted at the 2' position with a substituent selected from the group consisting of fluorine and chlorine.

2. Benzophenone derivative according to claim 1, wherein $R_1$ is a substituent selected from the group consisting of hydrogen and methyl and $R_2$ is a substituent selected from the group consisting of hydrogen, methyl and butyl.

* * * * *